(12) United States Patent
Narayanasa et al.

(10) Patent No.: US 12,005,218 B2
(45) Date of Patent: Jun. 11, 2024

(54) DEVICES AND METHODS FOR WARM GAS THERAPY

(71) Applicant: Yostra Labs Pvt Ltd, Bengaluru (IN)

(72) Inventors: Maruthy Kalburgi Narayanasa, Bengaluru (IN); Ram Mohan Rao, Bengaluru (IN); Sanjay Seetharama Sharma, Bengaluru (IN); Arunkumar Venkatesan, Bengaluru (IN); Vinayaka Nandalike Padmanabha, Bengaluru (IN)

(73) Assignee: YOSTRA LABS PVT LTD, Karnataka (IN)

( * ) Notice: Subject to any disclaimer, the term of this patent is extended or adjusted under 35 U.S.C. 154(b) by 1091 days.

(21) Appl. No.: 16/637,232

(22) PCT Filed: Aug. 8, 2018

(86) PCT No.: PCT/IN2018/050518
§ 371 (c)(1),
(2) Date: Feb. 6, 2020

(87) PCT Pub. No.: WO2019/030774
PCT Pub. Date: Feb. 14, 2019

(65) Prior Publication Data
US 2020/0230387 A1    Jul. 23, 2020

(30) Foreign Application Priority Data
Aug. 8, 2017   (IN) .............................. 201741028213

(51) Int. Cl.
*A61M 35/00*   (2006.01)
*A61H 33/06*   (2006.01)
(Continued)

(52) U.S. Cl.
CPC ........... *A61M 35/30* (2019.05); *A61H 33/063* (2013.01); *A61H 33/14* (2013.01); *A61M 1/90* (2021.05);
(Continued)

(58) Field of Classification Search
CPC ........ A61H 2033/061; A61H 2033/141; A61H 2033/143; A61H 2201/0103;
(Continued)

(56) References Cited

U.S. PATENT DOCUMENTS 7,140,367 B2 * 11/2006 White ................. A61M 16/024
128/203.26
11,129,954 B2 * 9/2021 Buswell ................ A61G 11/00
(Continued)

FOREIGN PATENT DOCUMENTS

EP       2255124 A1      12/2010
JP    2007 319618 A      12/2007
(Continued)

OTHER PUBLICATIONS

International Search Report and Written Opinion from corresponding International Application No. PCT/IN2018/050518, 10 pgs., dated Oct. 29, 2018.
(Continued)

*Primary Examiner* — Michael F Peffley
(74) *Attorney, Agent, or Firm* — Crowell & Moring LLP (57) ABSTRACT

Devices and method for warm gas therapy is provided. Device comprises a gas warmer assembly to warm a first gas to a temperature in a first temperature range to obtain warm first gas. The device comprises a first delivery unit that can deliver the warm first gas to a main treatment chamber which encloses a sub-treatment chamber to retain heat therein. A second delivery unit can receive a therapeutic gas from a gas supply. The second delivery unit comprises a first
(Continued)

portion and a second portion. The first portion substantially passes through the first delivery unit and therapeutic gas in the first portion is warmed by the warm first gas. The second portion delivers the warm therapeutic gas to a sub-treatment chamber. The sub-treatment chamber encloses a body part of a patient.

19 Claims, 8 Drawing Sheets

(51) Int. Cl.
    *A61H 33/14*     (2006.01)
    *A61M 1/00*     (2006.01)
(52) U.S. Cl.
    CPC .. *A61H 2033/061* (2013.01); *A61H 2033/141* (2013.01); *A61H 2033/143* (2013.01); *A61H 2201/0228* (2013.01); *A61H 2201/105* (2013.01); *A61H 2201/1642* (2013.01); *A61H 2201/5007* (2013.01); *A61H 2201/5043* (2013.01); *A61H 2201/5082* (2013.01); *A61M 2202/0208* (2013.01); *A61M 2202/0216* (2013.01); *A61M 2205/18* (2013.01); *A61M 2205/3368* (2013.01); *A61M 2205/362* (2013.01); *A61M 2205/3653* (2013.01); *A61M 2205/50* (2013.01); *A61M 2210/086* (2013.01)
(58) Field of Classification Search
    CPC .... A61H 2201/0176; A61H 2201/0228; A61H 2201/105; A61H 2201/1207; A61H 2201/164; A61H 2201/1642; A61H 2201/1688; A61H 2201/50; A61H 2201/5007; A61H 2201/5043; A61H 2201/5046; A61H 2201/5056; A61H 2201/5082; A61H 2201/5097; A61H 2205/12; A61H 33/14; A61H 35/006; A61M 1/90; A61M 1/94; A61M 2202/0208; A61M 2202/0216; A61M 2205/18; A61M 2205/3368; A61M 2205/362; A61M 2205/3653; A61M 2205/50; A61M 2210/086; A61M 35/30
    USPC .............................................. 607/96; 604/23
    See application file for complete search history.

(56) References Cited

U.S. PATENT DOCUMENTS

| | | |
|---|---|---|
| 2005/0261615 A1 | 11/2005 | Weston |
| 2010/0228183 A1 | 9/2010 | Sunnen |
| 2011/0040239 A1* | 2/2011 | Schneider ............. A61M 35/30 |
| | | 422/111 |
| 2012/0004600 A1* | 1/2012 | Nakamura ............. A61H 33/14 |
| | | 604/24 |
| 2014/0046247 A1 | 2/2014 | Nakamura |
| 2016/0143771 A1 | 5/2016 | Swyer et al. |

FOREIGN PATENT DOCUMENTS

| | | |
|---|---|---|
| JP | 3 150690 U | 5/2009 |
| WO | WO 2001089633 A2 | 11/2001 |
| WO | WO 2009112726 | 9/2009 |

OTHER PUBLICATIONS

International Preliminary Report on Patentability from corresponding International Application No. PCT/IN2018/050518, 8 pgs., dated Feb. 11, 2020.
Extended European Search Report regarding 18 843 631.5 dated Mar. 23, 2021, 7 pages.

* cited by examiner

DEVICES AND METHODS FOR WARM GAS THERAPY

REFERENCE TO EARLIER FILED APPLICATIONS

This application is the national phase of International Application No. PCT/IN2018/050518, filed Aug. 8, 2018, and claims the benefit of Indian Application No. 201741028213, filed Aug. 8, 2017, the disclosures of which are incorporated, in their entirety, by this reference.

TECHNICAL FIELD

The present subject matter relates, in general, to devices and methods for warm gas therapy and, in particular, to devices and methods for delivery of warm gas for dermatological and sub-cutaneous tissue treatment.

BACKGROUND

Medical gas therapy is the administration of medical gases to a patient suffering from a disease or disorder. Medical gases used in medical gas therapy range from traditional gases, such as oxygen, carbon dioxide, and nitrous oxide, to gaseous cellular messenger molecules, such as nitric oxide and hydrogen sulfide. Common forms of medical gas therapies include carboxytherapy and oxygen therapy.

Carboxytherapy is the administration of carbon dioxide in therapeutic doses to a patient. Carboxytherapy is useful in the treatment of dark circles of the eyes, cellulitis reduction, and non-surgical fat reduction of the body. On the other hand, oxygen therapy is a treatment that provides a patient with extra oxygen. A method of oxygen therapy is by the usage of hyperbaric oxygen. Hyperbaric Oxygen Therapy (HBOT) is the administration of oxygen to a patient at a pressure greater than atmospheric pressure. Although carboxytherapy and oxygen therapy are commonly used, other forms of therapy using other gases may also be used.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

FIG. 3(*a*) illustrates details of an example gas warmer assembly of the device, in accordance with an implementation of the present subject matter.

FIG. 3(*b*) illustrates details of an example gas warmer assembly of the device, in accordance with an implementation of the present subject matter.

DETAILED DESCRIPTION

Using therapeutic or medical gases for treatment is a relatively unexplored field of therapy. Oxygen therapy using Hyperbaric Oxygen Therapy (HBOT) for treatment of wounds and serious infections remains one of the most well-known forms of medical gas therapy. During HBOT a patient is placed in an airtight chamber and subjected to oxygen at pressure higher than atmospheric pressure. During HBOT, the entirety of the patient's body is subjected to high pressure. The patient may undergo mild discomfort due to high pressure used and airtight nature of HBOT chamber. The patient may also experience some side-effects, such as pressure related trauma to the ears, decompression sickness, and the like. Further, HBOT is expensive and is, typically, used only in case of serious infections. The present subject provides a device for delivery of warm therapeutic gas. In an example, the warm therapeutic gas may be used for dermatological and sub-cutaneous tissue treatment. The present subject matter, on the one hand, provides localized delivery of therapeutic gas and, on the other hand, reduces discomfort caused to the patient during treatment. In one example, delivery of warm therapy gases through a treatment bag may be used to treat a wound on the foot where the treatment envelope covers the whole leg. In addition, more targeted treatment of the infection or wound may be preferable. This can help to maintain accurate gas concentration, time of exposure, temperature, and humidity in the vicinity of the treatment area.

Warm therapy gas can be used for treatment of conditions not limited to dermatological and subcutaneous tissue treatment. Although the description is provided with reference to treatment of diabetic foot ulcer as an example, it may be understood that the device may be used to treat other disorders, such as bed sores, nail afflictions, wounds, ulcers, burns, cosmetic conditions, and the like, and similar devices and methods as taught by the present subject matter, albeit with a few variations, may be used for the treatment of such disorders as may be understood by a person skilled in the art.

Wound healing is a step-wise replacement of extracellular matrix (ECM), which forms a bulk of the dermal layer of the skin. Wound healing is an innate mechanism which works reliably most of the time, but at times can be affected by certain disorders, such as diabetes mellitus. Diabetes mellitus is a metabolic disorder that affects normal steps of wound healing process by delaying formation of mature connective tissue and blood vessels. Diabetic patients also suffer from diabetic neuropathy, i.e., loss of feeling in toes, feet, legs, and arms. Blisters, sores, and other injuries, especially in the lower extremities, such as feet and toes, usually go unnoticed. Such blisters, sores, and other injuries are called diabetic foot ulcers. Since wound healing is impaired in diabetic patients, diabetic foot ulcers are prone to infections. Diabetic foot ulcer is a major complication of diabetic mellitus. Diabetic foot ulcers occur in 15% of people with diabetes and are responsible for 84% of lower leg amputations due to infections of ulcers. In one implementation, the device of the present subject matter may be used for treatment of diabetic foot ulcer.

Another form of ulcer that maybe treated by the device of the present subject matter is decubitus ulcer. Decubitus ulcer, commonly called bed sores, is a condition that arises when a person remains in bed or a wheelchair for a prolonged period of time. The pressure exerted upon skin points which are in contact with bed, wheelchair, or any other surface, compresses the dermal arterioles which supply oxygen to the skin points. This compression prevents diffusion of oxygen to the compressed skin points. Consequently, skin tissue suffers from oxygen starvation and impaired skin resilience, eventually leading to breakdown of the skin itself forming the decubitus ulcer. The ulcer formed slowly expands and maybe infected with a myriad of pathogens. The infection may then spread to the bones, causing osteomyelitis. The device of the present subject matter may be used for the treatment of decubitus ulcer and improve healing of the ulcer by delivery of therapeutic gas to the ulcer.

The device of the present subject matter may also be used for the treatment of war wounds. Healing of war wounds is complicated due to presence of debris, such as shrapnel and other foreign bodies, in the wound. Such debris provides spots for infections to be initiated. The infections may further be aggravated by hot weather and high humidity, which are common environmental conditions in war zones. The device of the present subject matter may also be used for the treatment of war wounds.

The device of the present subject matter may also be used for the treatment of thermal burns. Thermal burns are often classified as first degree, second degree, and third-degree burns. First degree burns are superficial and are associated with swelling and pain. Second degree burns are associated with dermal damage, along with epidermal damage, and are associated with formation of blisters and ulceration. Third degree burns usually affect muscles, tissues, and bones. Third degree burns are especially prone to secondary infections which are hard to treat due to the extent of skin damage.

The device of the present subject matter may also be used for the treatment of nail afflictions. Certain fungi, such as *Candida albicans*, cause nail afflictions that can be treated by the device of the present subject matter. *Candida albicans* causes a condition in nails because of which the nails start paining. It is accompanied by swelling in nail folds and transverse grooving of nails, eventually leading to loss of the nail itself. Another common fungal infection is tinea pedis, commonly called Athlete's foot, caused by dermatophyte fungal species of *Trichophyton*. Topical antifungal medicines are not effective against these infections and the fungus quickly become resistant to topical medicines. Systemic antibiotics have noxious side effects.

The device of the present subject matter may also be used to improve health and aesthetic quality of skin. The benefits may be enhanced by delivery of anti-aging serum to the skin along with therapeutic gas. The device of the present subject matter may also be used for the treatment of postoperative external wounds. The device of the present subject matter may also be used for the treatment of wounds associated with chemotherapy.

The above mentioned are some example conditions that can be treated with the help of the device of the present subject matter. In general, as will be understood, the device of the present subject matter can be used for any kind of dermatological treatment, sub-cutaneous tissue treatment, wounds, burns, and the like.

The device of the present subject matter comprises a gas warmer assembly to warm a first gas to a temperature in a first temperature range to obtain warm first gas. The gas warmer assembly comprises a heater and a microprocessor. The heater warms the first gas to the temperature in the first temperature range. The microprocessor controls the heater.

The device comprises a first delivery unit and a second delivery unit. The first delivery unit can be coupled to the gas warmer assembly to deliver the warm first gas received from the gas warmer assembly to a main treatment chamber. The second delivery unit is to receive a therapeutic gas from a gas supply. The second delivery unit comprises a first portion and a second portion. The first portion substantially passes through the first delivery unit. The warm first gas warms the therapeutic gas in the first portion to obtain warm therapeutic gas. The second portion is to deliver the warm therapeutic gas to a sub-treatment chamber.

The device comprises the main treatment chamber associated with a first sensor to measure and communicate a main treatment chamber temperature to the microprocessor. The device further comprises the sub-treatment chamber to enclose a site of a patient for treatment. The main treatment chamber encloses the sub-treatment chamber to retain heat in the sub-treatment chamber. The sub-treatment chamber is associated with a second sensor to measure and communicate a sub-treatment chamber temperature to the microprocessor. The device further comprises a remote-control unit operably connected with the microprocessor to control parameters of the gas warmer assembly based on user input.

The device of the present subject matter thus facilitates in creating the sub-treatment chamber with targeted delivery of warm therapeutic gases. The warm therapeutic gas is precisely delivered to the site of the patient which requires treatment. The precise delivery of the warm therapeutic gas increases blood supply to that site. The increased blood supply enables faster healing. Additionally, using warm therapeutic gas which has intrinsic antibiotic activity, such as oxygen, further destroys microorganisms and reduces the degree of infection. Increase in temperature of the site by exposure to warm therapeutic gas may also allow for better absorption of externally delivered antibiotics and other bioactive agents, such as anti-aging serums. Further, by using the sub-treatment chamber for dermatological and sub-cutaneous treatment parameters, such as temperature, delivery dose, and the like, can be accurately maintained.

In one example, the device of the present subject matter can include a bioactive agent delivery system to allow mixing and delivery of bioactive agents, such as antibiotics, enzymes, anti-aging serums, growth factor agents, and the like, with the warm gas for targeted treatment of the site or body part of the patient. Thus, the treatment efficacy can be further enhanced. Further, as the sub-treatment chamber help in targeted delivery, quantity of bioactive agents required for treatment is reduced. This reduces cost of treatment and makes the treatment affordable even in resource-constrained areas. In another implementation, the bioactive agent may be applied on the site of treatment before it is subjected to warm gas treatment. In an example, the device can further comprise a Negative Pressure Wound Treatment (NPWT) system to remove exudates secreted around the body part being treated.

The device of the present subject matter is portable. The device may be used in any setting, such as home, hospital, in a remote location, and the like. The device can be constructed using easily available and economic components, thereby ensuring that the cost of the device is low. The device of the present subject matter is simple to operate and is, additionally, low maintenance. The treatment chambers, namely the main treatment chamber and the sub-treatment chamber, can be made collapsible and disposable to further enhance mobility and ease of use, and ensure prevention of cross-infection between patients.

In addition to treating dermatological conditions and sub-cutaneous tissue, the device may also be used to improve health and aesthetic appearance of skin. This can be achieved by using humidified oxygen with concentration of oxygen as high as 90% as the warm gas.

The above and other features, aspects, and advantages of the subject matter will be better explained with regard to the following description and accompanying figures. It should be noted that the description and figures merely illustrate the principles of the present subject matter along with examples described herein and, should not be construed as a limitation to the present subject matter. It is thus understood that various arrangements may be devised that, although not explicitly described or shown herein, embody the principles of the present disclosure. Moreover, all statements herein reciting principles, aspects, and examples thereof, are intended to encompass equivalents thereof. Further, for the sake of simplicity, and without limitation, the same numbers are used throughout the drawings to reference like features and components.

Figure 1:
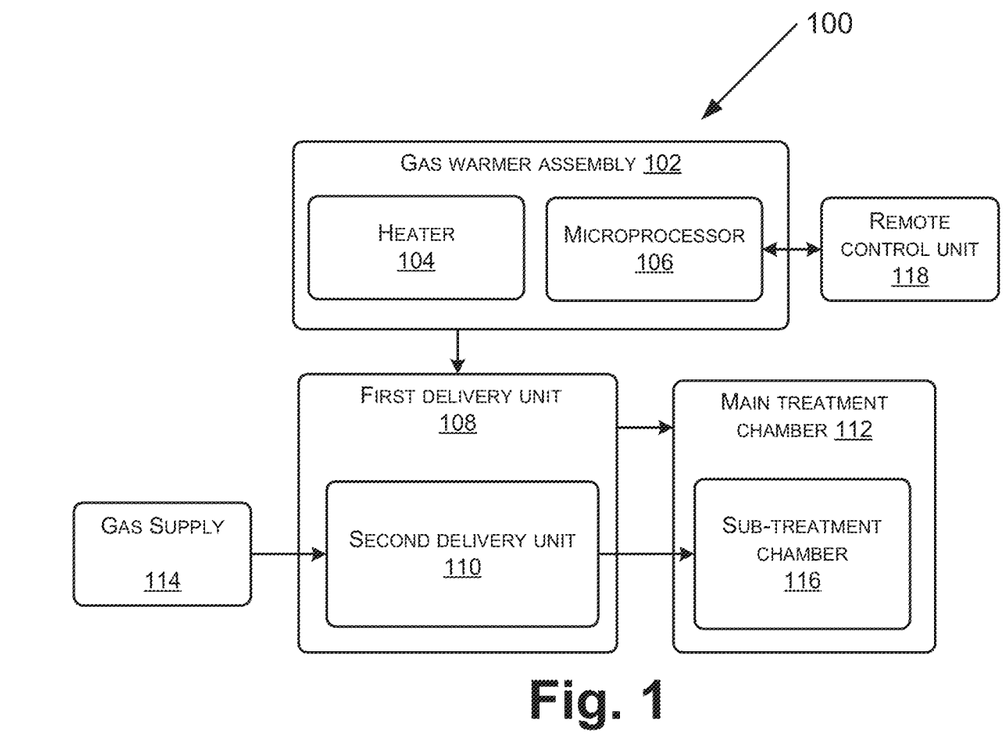
FIG. 1 illustrates a block diagram of a device for warm gas therapy, in accordance with an implementation of the present subject matter.

FIG. 1 illustrates a block diagram of a device 100 for delivery of therapeutic gas, in accordance with an implementation of the present subject matter. The device 100 can be used for treatment of a body part of a patient. The device 100 includes a gas warmer assembly 102 that can warm a first gas to a temperature in a first temperature range to obtain warm first gas. In one example, the first gas is air. In said example, the gas warmer assembly 102 can draw atmospheric air into the gas warmer assembly 102 to warm the first gas. In one example, the first temperature range is 39-42° C.

The gas warmer assembly 102 includes a heater 104 and a microprocessor 106. The heater 104 can heat the first gas to the temperature in the first temperature range. The heater 104 can be one of an electric heater, a conduction heater, a convection heater, and a radiation heater. In one example, the heater 104 is a Nichrome heating element. It is to be understood that the heater 104 may have other configurations and arrangements as will be explained later. The microprocessor 106 can control the heater 104. In one example, the microprocessor 106 can control the heater 104 to change a working state of the heater 104, i.e., to switch on or switch off the heater 104.

The device 100 can comprise a first delivery unit 108 and a second delivery unit 110. The first delivery unit 108 can be coupled to the gas warmer assembly 102 to receive the warm first gas from the gas warmer assembly 102. The first delivery unit 108 can deliver the warm first gas to a main treatment chamber 112. In one example, the first delivery unit 108 can be detachably coupled with the gas warmer assembly 102 and the main treatment chamber 112. The first delivery unit 108 can comprise a diffuser to diffuse the warm first gas in the main treatment chamber 112 as will be explained later.

The second delivery unit 110 can receive a therapeutic gas from a gas supply 114. The therapeutic gas can be a gas selected from the group consisting of oxygen, ozone, and combination, thereof. The second delivery unit 110 can comprise a first portion and a second portion. The second delivery unit 110 can be a flexible pipe comprising the first portion provided inside the first delivery unit 108 and the second portion provided outside the first delivery unit 108, respectively. The first portion substantially passes through the first delivery unit 108. The warm first gas warms the therapeutic gas in the first portion to obtain warm therapeutic gas. Therefore, the therapeutic gas is warmed due to co-current flow of the warm first gas and the therapeutic gas in the first portion of the second delivery unit. The second portion can deliver the warm therapeutic gas to a sub-treatment chamber 116. In one example, the second portion can be detachably coupled to the sub-treatment chamber 116. In another example, the first portion and the second portion can be detachably coupled to the first delivery unit 108.

The main treatment chamber 112 can be associated with a first sensor. The first sensor can measure and communicate a main treatment chamber temperature to the microprocessor 106. The main treatment chamber 112 can enclose the sub-treatment chamber 116 to retain heat in the sub-treatment chamber 116 more effectively. The sub-treatment chamber 116 can enclose a site of the patient for treatment. The sub-treatment chamber 116 can be associated with a second sensor to measure and communicate a sub-treatment chamber temperature to the microprocessor 106. The first sensor and the second sensor may be wired sensors or wireless sensors. The microprocessor 106 can control the heater 104 based on the main treatment chamber temperature and the sub-treatment chamber temperature as will be explained later.

A remote-control unit 118 can be operably connected with the microprocessor 106 to control parameters of the gas warmer assembly 102 based on user input. The remote-control unit 118 may communicate with the microprocessor 106 either wirelessly or through a wired arrangement, as will be understood by a person skilled in the art. For brevity, the communication protocols and methods have not been described.

In one example, the remote-control unit 118 provides the patient the ability to change a working state of the heater 104 for example, in case of an emergency. The patient may change the working state of the heater 104 to one of ON and OFF. In another example, the remote-control unit 118 may also provide the patient the ability to remotely switch on or switch off the gas warmer assembly 102. In another example, the remote-control unit 118 provides the patient the ability to only switch on or switch off the gas warmer assembly 102 while the operator has the ability to set gas warmer assembly 102 parameters, such as, threshold temperature, number of cycles, duration of treatment, and the like. In one example, the operator is a medical professional.

In operation, the gas warmer assembly 102 receives the first gas to obtain the warm first gas. The warm first gas can then be received by the first delivery unit 108 which further delivers the warm first gas to the main treatment chamber 112. The second delivery unit 110 can receive the therapeutic gas from the gas supply 114. The therapeutic gas can be warmed by the warm first gas in the first portion of the second delivery unit 110. The second delivery unit 110 can then deliver the warm therapeutic gas to the sub-treatment chamber 116. In one implementation, the device 100 can include or can be used with a bioactive agent delivery system (not shown in this figure) to allow mixing and delivery of bioactive agents, such as antibiotics, insulin, serums, and the like, with the warm therapeutic gas for targeted treatment of the body part of the patient. In one implementation, the device 100 can include or can be used with a Negative Pressure Wound Treatment (NPWT) system to remove exudates from the body part being treated. The various parts and operation of the device have been elaborated in FIG. 2.

Figure 2:
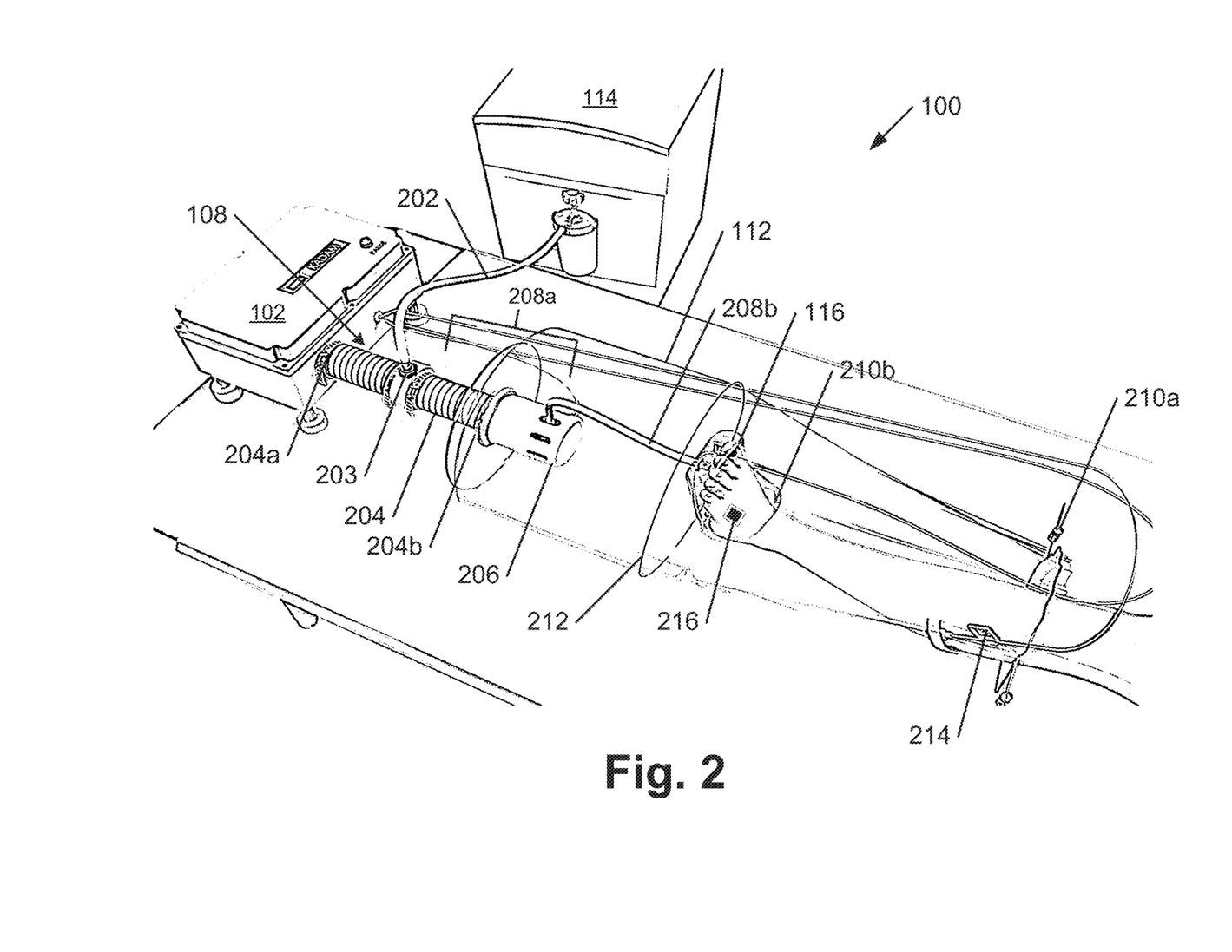
FIG. 2 illustrates a schematic of the device during treatment, in accordance with an implementation of the present subject matter.

FIG. 2 illustrates a schematic of the device 100 during use, in accordance with an implementation of the present subject matter. The schematic, as shown in FIG. 2, depicts treatment of diabetic foot ulcer by exposure of the diabetic foot ulcer to warm gas. However, it will be understood that the device 100 can be used for the treatment of any other condition, including but not limited to dermatological condition and any disorder of sub-cutaneous tissue.

The device 100 can comprise the gas supply 114. The gas supply 114 supplies the therapeutic gas to the device 100. In an example, the gas supply 114 may be a gas cylinder. In another example, the gas supply 114 may be a gas generator, such as an oxygen generator or an ozone generator. In yet another example, the gas supply 114 may be a gas concentrator, such as an oxygen concentrator. In another example, which is not shown herein but will be understood, the gas supply 114 may be external to the device 100. In such a case, the gas supply 114 may be any gas source, such as a centralized hospital gas source, a gas cylinder, and the like. The gas supply 114 may also mix two or more gases, such as ozone and oxygen, before supplying it to the gas warmer assembly 102. The therapeutic gas from the gas supply 102 is received by the second delivery unit 110 through a hose 202. In one example, the hose 202 is fabricated from rubber. In another example, the hose 202 may be fabricated from any insulating material. Flow rate of the therapeutic gas can be maintained at the desired value using valves and flow meters, as will be understood.

The hose 202 can be coupled to the device 100 at the first delivery unit 108, for example, at a mid-portion of the first delivery unit 108. The hose 202 may be coupled to the first delivery unit 108 using coupler 203.

The first delivery unit 108 can comprise a tube 204. The tube 204 can comprise a first end 204a and a second end 204b. The first end 204a can be coupled to the gas warmer assembly 102 to receive the warm first gas from the gas warmer assembly 102. The second end 204b may be enclosed in the main treatment chamber 112. The first delivery unit 108 can also comprise a diffuser 206 provided on the second end 204b of the tube 204 to diffuse the warm first gas in the main treatment chamber 112. The diffuser 206 can be associated with a third sensor to measure and communicate a diffuser outlet temperature to the microprocessor 106. The warm first gas in the first delivery unit 108 can warm the therapeutic gas received from the gas supply 114.

In the first delivery unit 108, the coupler 203 can couple the hose 202 to a first portion 208a of the second delivery unit 110. In one example, the first portion 208a passes through and can be substantially coaxial to the tube 204 of the first delivery unit 108. The first portion 208a can, therefore, receive the therapeutic gas from the hose 202. The therapeutic gas in the first portion 208a can be warmed by the first warm gas to obtain the warm therapeutic gas. The second delivery unit 110 can further comprise a second portion 208b coupled to the first portion 208a. The second portion 208b can deliver the warm therapeutic gas to the sub-treatment chamber 116. The second portion 208b can be introduced into the sub-treatment chamber 116 through an aperture provided in the sub-treatment chamber 116.

As shown in FIG. 2, the main treatment chamber 112 encloses the sub-treatment chamber 116. This configuration allows for maintaining heat during treatment for a longer period of time. Further, as the sub-treatment chamber 116 is used for delivering the warm therapeutic gas, there is a significant reduction in amount of therapeutic gas required. This further helps in making the device 100 more economical. Further, as the sub-treatment chamber 116 is a smaller space than the main treatment chamber 112, it is possible to provide targeted and localized delivery. Further, it is also possible to maintain accurate temperatures, humidity, and concentrations.

In an example, the main treatment chamber 112 and the sub-treatment chamber 116 may be a treatment bag. The treatment bag can be a disposable, collapsible bag which may be disposed after one use to prevent cross-infections. In another example, the treatment bag may be fabricated from polythene. In another example, the treatment bag can be fabricated from bio-degradable material.

The treatment bag corresponding to the main treatment chamber 112 and the sub-treatment chamber 116 can comprise a chord seal 210a, 210b, respectively. The chord seal 210a, 210b, hereinafter referred to as chord seal 210, can be used to seal the site the patient for treatment and to restrict escape of gas and, consequently, to maintain the main treatment chamber temperature and the sub-treatment chamber temperature. In one example, the treatment bag can have the chord seal 210 a single end, for example, while treating a diabetic foot ulcer on a big toe. In another example, the treatment bag can have multiple chord seals. For example, for treatment of a wound on an ankle, the treatment bag can have two chord seals at two ends of the treatment bag to isolate the ankle from the rest of the foot. In one example, the treatment bag corresponding to the sub-treatment chamber 116 can have two chord seals 210 at opposite ends and the treatment bag corresponding to the main treatment chamber 112 can have a single chord seal 210.

In one example, in order to prevent the treatment bag surface from touching the body part, the treatment bags may be first inflated with warm first gas or warm therapeutic gas before the site for treatment is introduced into the treatment bag. For example, the treatment bag corresponding to the main treatment chamber 112 is inflated with the warm first gas, followed by inflation of the treatment bag corresponding to the sub-treatment chamber 116 before introducing the body part of the user.

In another example, in order to prevent the treatment bag surface from touching the body part, the treatment bag can be provided with shape retainers 212 that hold the treatment bag in shape and prevent it from collapsing. For example, the shape retainer 212 can be a ring-like structure placed inside the treatment bags to prevent collapse of the treatment bags.

In one example, the main treatment chamber 112 and/or the sub-treatment chamber 116 can comprises an exhaust for exhaust of the warm first gas and the warm therapeutic gas, respectively. In another example, the main treatment chamber 112 and/or the sub-treatment chamber 116 do not have an exhaust and the warm first gas and the warm therapeutic gas escapes from the chord seals 210 of the respective treatment chambers.

The device 100 can further include the first sensor 214 and the second sensor 216. The first sensor 214 can be provided in the main treatment chamber 112. The first sensor 214 may be coupled to the body part of the patient enclosed by the main treatment chamber 112 but outside the sub-treatment chamber 116. In another example, where the first sensor 214 is a wired sensor, the first sensor 214 may be suspended in the main treatment chamber 112 to measure and communicate the main treatment chamber temperature to the microprocessor 106.

The second sensor 216 can be provided in the sub-treatment chamber 116. The second sensor 216 may be coupled to the body part substantially close to the site of treatment of the patient enclosed by the sub-treatment chamber 116. In another example, where the second sensor 216 is a wired sensor, the second sensor 216 may be suspended in the sub-treatment chamber 116 to measure and communicate the sub-treatment chamber temperature to the microprocessor 106.

Figure 3A:
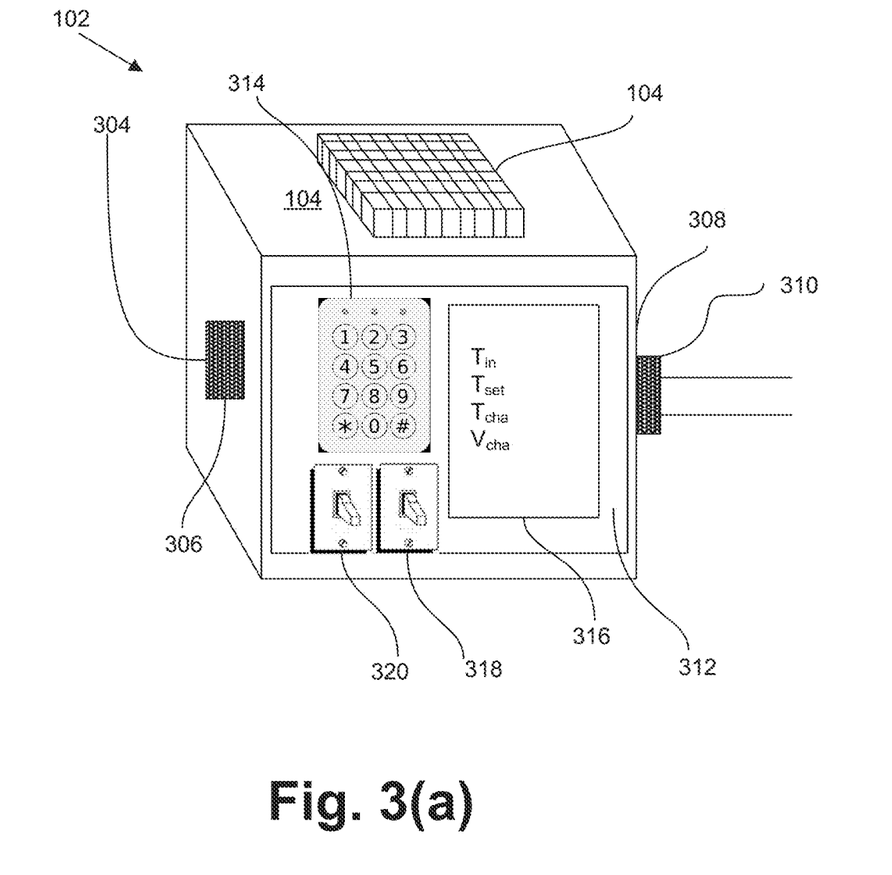

FIG. 3(a) further illustrates an example gas warmer assembly 102 in detail, in accordance with an implementation of the present subject matter. The gas warmer assembly 102 includes a gas warmer inlet 304 associated with a gas warmer inlet temperature sensor 306. In an example, the gas warmer assembly 102 can have more than one gas warmer inlet 304. The gas warmer inlet 304 can be associated with a fan to draw the first gas, namely air, from the surroundings.

The gas warmer inlet temperature sensor 306 measures and provides an inlet temperature of the first gas entering the gas warmer assembly 102 to the microprocessor 106 (not shown in FIG. 2). The gas warmer assembly 102 can comprise the heater 104 which may be, but is not restricted to, an electrical heater, a convective heater, a conductive heater, or a radiant heating source. The gas warmer assembly 102 further comprises a gas warmer outlet 308.

The gas warmer outlet 308 may be coupled to the first delivery unit 108. The gas warmer outlet 308 can be associated with a gas warmer outlet temperature sensor 310. The gas warmer outlet temperature sensor 310 can measure and provides an outlet temperature of warm first gas at the gas warmer outlet 308 to the microprocessor 106.

The gas warmer assembly 102 can further include slots for detachably coupling the first sensor, the second sensor, and the third sensor. In another example, when wireless sensors are used, the gas warmer assembly 102 does not include slots for coupling the first sensor, the second sensor, and the third sensor.

Further, as shown in FIG. 3(a), the gas warmer assembly 102 can be a box or housing comprising the microprocessor 106 (not shown in FIG. 3(a)) and the heater 104. A face 312 of the gas warmer assembly 102 can comprise an input module 314 to receive input parameters. The input module 314 can include a keypad, a touch-screen input, and the like, as will be understood. The input parameters may include a first threshold temperature and a second threshold temperature. The first threshold temperature and the second threshold temperature can be used by the microprocessor 106 to turn on and turn off the heater 104 as will be explained later. The input parameters may also include duration of treatment, number of cycles, and the like.

The gas warmer assembly 102 can also include a display module 316 which displays values of input parameters, main treatment chamber temperature, sub-treatment chamber temperature, the diffuser outlet temperature, time duration remaining, and the like. The first threshold temperature and the second threshold temperature can be set using a set switch 318 placed on the face 312 of the gas warmer assembly 102. The gas warmer assembly 102 can also comprise a power switch 320 to change a working state of the gas warmer assembly 102, i.e., switch on and switch off the gas warmer assembly 102. The gas warmer assembly 102 may also comprise a timer (not shown) to indicate duration of treatment and to provide an alert indicating end of duration of treatment. The timer may also be used to set the time of treatment and automatically switch OFF the heater 104 on expiry of the set time.

In operation, the operator can set the first threshold temperature, the second threshold temperature, and a third threshold temperature using the input module 314 and the set switch 318. The heater 104 can heat the first gas to the temperature in the first temperature range. The microprocessor 106 can receive temperature measured by the first sensor, the second sensor, and the third sensor. Based on the comparison between the main treatment chamber temperature and sub-treatment chamber temperature, the microprocessor 106 can be configured to switch on or switch off the heater 104. By using two threshold temperatures, namely the first threshold temperature and the second threshold temperature, to control the working state of the heater 104, it is possible to reduce the number of times the heater 104 may be switched on and off. Additionally, this also ensures safety and preventing of overheating, while ensuring that adequate temperature is maintained in the main treatment chamber 112 and the sub-treatment chamber 116. Further, to improve safety, the microprocessor 106 can compare the diffuser outlet temperature with the third threshold temperature and can be configured to switch off the heater 104 if the diffuser outlet temperature exceeds the third threshold temperature.

Figure 3B:
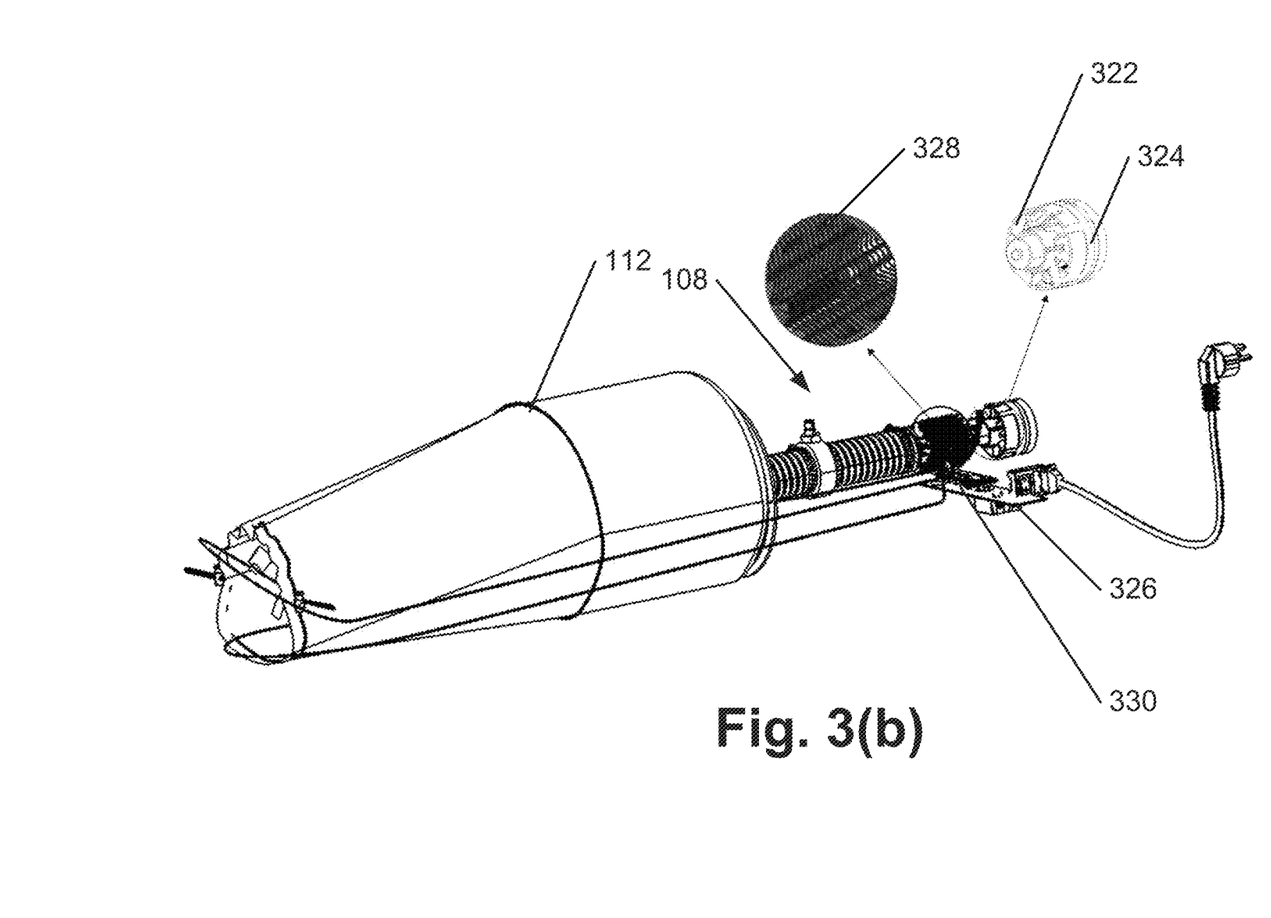

FIG. 3(b) depicts a perspective view of internal components of another gas warmer assembly 102, the first delivery unit 108, and the main treatment chamber 112, in accordance with an implementation of the present subject matter. The example gas warmer assembly 102 as shown in FIG. 3(b) can have a fan 322 to draw air, i.e., the first gas into the gas warmer assembly 102. The fan 322 may be associated with the gas warmer inlet (not shown). The fan 322 can be provided in a fan enclosure 324.

The gas warmer assembly 102 can also comprise a buzzer (not shown) to provide an alarm when at least one of the main treatment chamber temperature and the sub-treatment chamber temperature measured by the first sensor 214 and the second sensor 216 is more than the first threshold temperature. In one example, the gas warmer assembly 102 can include a switching element 328 to cut-off power supply to the heater 104 in case one of main treatment chamber temperature or the sub-treatment chamber temperature exceeds the first threshold temperature. In an example, the switching element 328 can be a thermostat. The thermostat can be a bimetallic strip which disconnects when one of main treatment chamber temperature or the sub-treatment chamber temperature exceeds the first threshold temperature and reconnects the heater 104 to the power supply when one of main treatment chamber temperature or the sub-treatment chamber temperature falls below threshold temperatures.

The gas warmer assembly 102 can also include a solid-state relay (SSR) (not shown) to ensure precise control of the main treatment chamber temperature and the sub-treatment chamber temperature. The SSR can receive signals from the microprocessor 106 and based on the received signals can control the heater 104. Electrical components, such as the heater 104, buzzer, the thermostat 328, the SSR and the like can be mounted on a Printed Circuit Board (PCB) 330. In one example, the heater 104 can be a Nichrome heating element. Other examples of the heater 104 are explained further.

Figure 4:
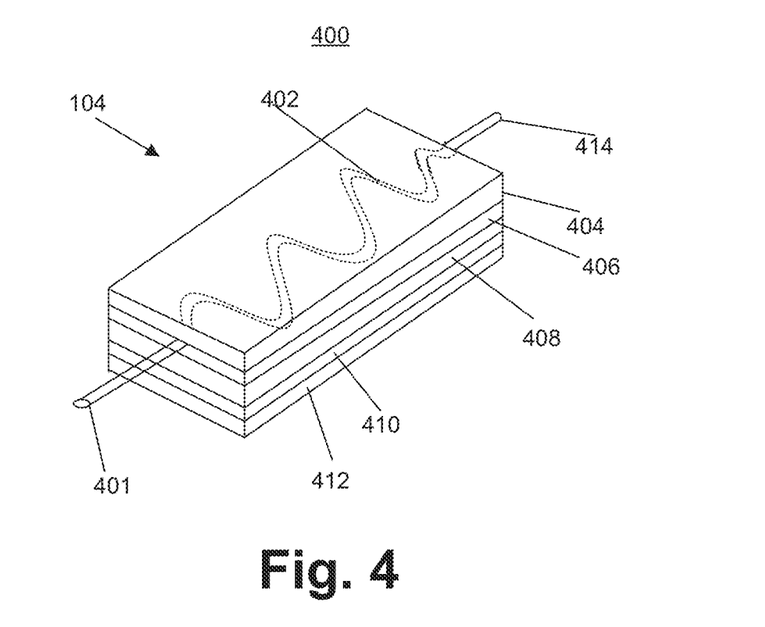
FIG. 4 illustrates an assembly of a heater, in accordance with an implementation of the present subject matter.

FIG. 4 illustrates an assembly 400 of the heater 104, in accordance with an implementation of the present subject matter. The assembly 400 comprises a heater inlet 401 to receive the first gas and a coil slot 406 sandwiched between aluminum plates 404 and 408. The coil slot 406 comprises a copper coil 402 to receive the first gas from the heater inlet 401. The first gas received by the heater inlet 401 flows through the copper coil 402. The heater 104, as shown in assembly 400, also comprises a heating element 410. The sandwiched structure, comprising the coil slot 406 and aluminum plates 404 and 408, is stacked over the heating element 410. The heating element 410 warms the first gas flowing through the copper coil 402. The heating element 410 can be stacked over another aluminum plate 412. The assembly 400 can also comprises a heater outlet 414 that provides warm first gas from the heater 104. The assembly 400 of the heater 104 prevents direct contact between heating element 410 and the first gas ensuring safety of usage when the gas used for treatment is combustible, such as oxygen. In an example, the heating element 410 is a 750 W heating element.

Figure 5:
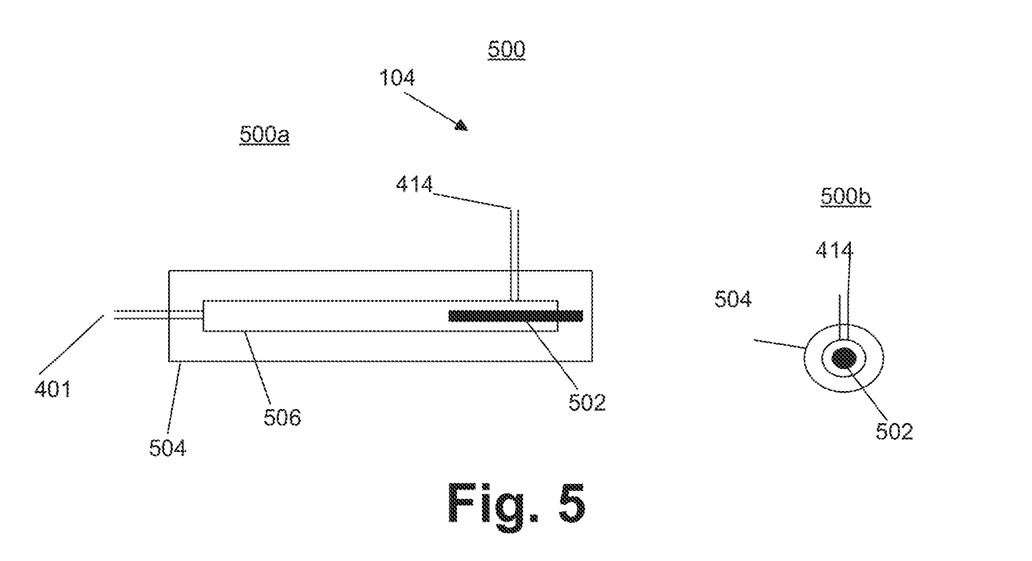
FIG. 5 illustrates an assembly of yet another heater, in accordance with an implementation of the present subject matter.

FIG. 5 illustrates an assembly 500 of yet another heater 104, in accordance with an implementation of the present subject matter. FIG. 5 illustrates a side view of the assembly 500. The assembly 500 comprises the heater inlet 401 to receive the first gas and a copper coil 506 to receive the first gas from heater inlet 401. The received first gas flows through the copper coil 506. The assembly 500 also comprises a heating element 502. The heating element 502 warms the first gas flowing through the copper coil 506. The assembly 500 also comprises an insulating jacket 504. The insulating jacket 504 encloses the copper coil 506 and the heating element 502. The assembly 500 also comprises the heater outlet 414 to provide warm first gas from the heater 108. The assembly 500 provides for direct contact with of the first gas with the heating element 502 ensuring faster heating and lower heat loss. FIG. 500b illustrates front view of assembly 500. In an example, the heating element is a 25 W heating element.

Figure 6:
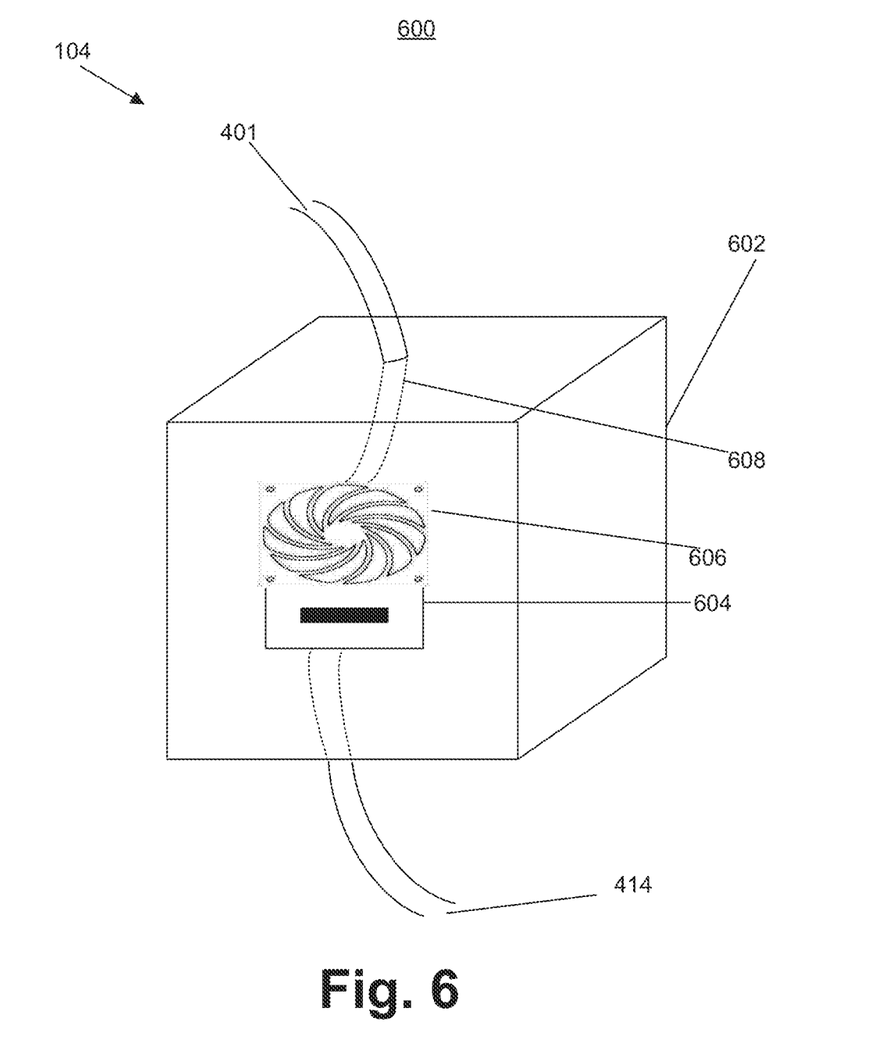
FIG. 6 illustrates an assembly of yet another heater, in accordance with an implementation of the present subject matter.

FIG. 6 illustrates an assembly 600 of yet another heater 104, in accordance with an implementation of the present subject matter. The assembly 600 comprises the heater inlet 401 to receive the first gas and a copper coil 608 to receive the first gas from the heater inlet 401. The received first gas flows through the copper coil 608. The assembly 600 also comprises a heating element 604. The heating element 604 warms the first gas flowing through the copper coil 608. The assembly 600 also comprises a fan 606 to dissipate heat in the gas warmer assembly 102. An insulating box 602 encloses the copper coil 608, the heating element 604, and the fan 606. The assembly 600 also comprises heater outlet 414 to provide warm gas from the heater 104. The assembly 600 provides for efficient heat dissipation and prevents over-heating of gas warmer assembly 102. In an example, the fan 606 is a 12V fan and the heating element 604 is a 25 W heating element.

Figure 7:
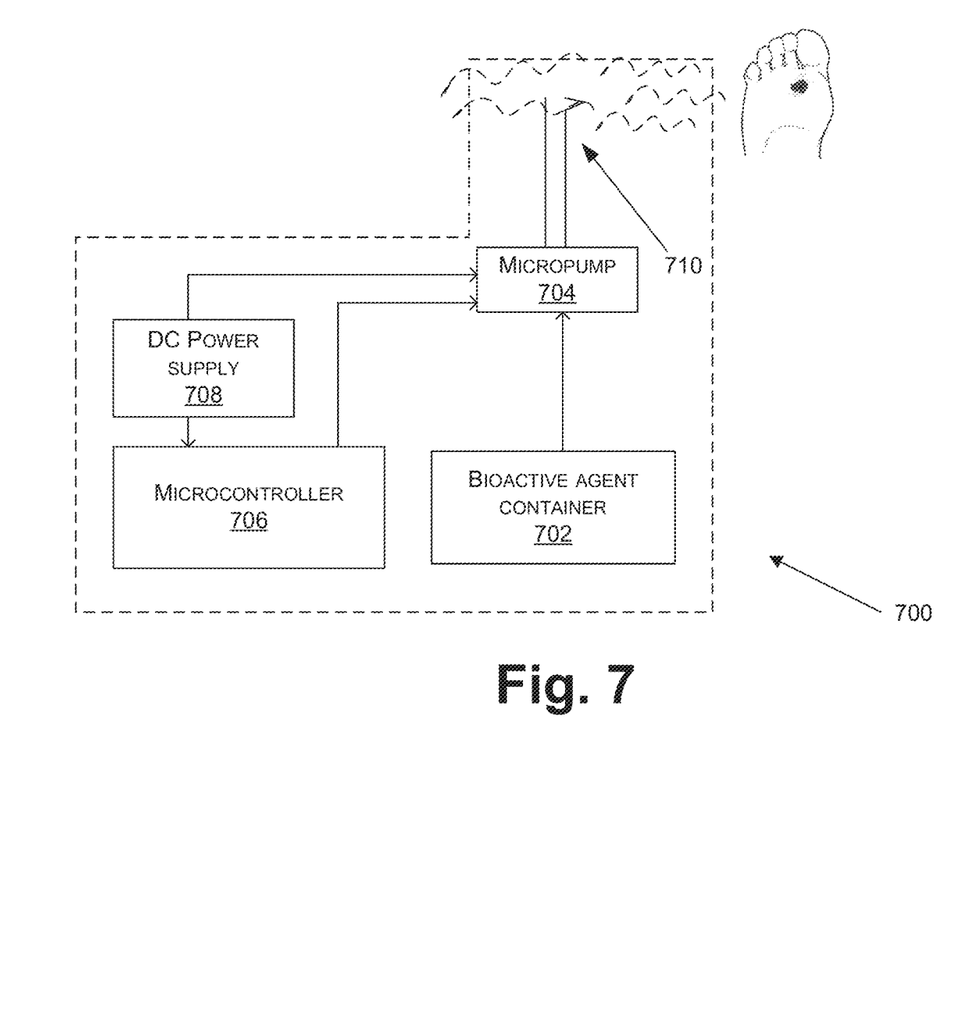
FIG. 7 illustrates schematic of a bioactive agent delivery system, in accordance with an implementation of the present subject matter.

While the heater 104 heats the first gas, the therapeutic gas is warmed by the warm first gas. The body part of the patient can be then exposed to the warm therapeutic gas in the sub-treatment chamber 116. For dermatological and sub-cutaneous treatment of the body part may be enhanced by introducing a bioactive agent in the sub-treatment chamber 116. FIG. 7 illustrates a schematic of a bioactive agent delivery system 700, in accordance with an implementation of the present subject matter.

The bioactive agent delivery system 700 is used to provide metered delivery of bioactive agent. The bioactive agent delivery system 700 can comprise a bioactive agent container 702 to hold the bioactive agent, a micropump 704, and a microcontroller 706. The micropump 704 can pump the bioactive agent from the bioactive agent container 702. The microcontroller 706 can control the micropump 704 to pump metered doses of the bioactive agent periodically. The micropump 704, can be controlled by microcontroller 706 and can pump pre-determined quantity of bioactive agent at pre-determined time intervals. In an example, the pre-determined quantity and pre-determined time interval is set by the operator in the gas warmer assembly 102. In an example, the microcontroller 706, consequent to communication with the microprocessor 106 of the gas warmer assembly 102, controls the micropump 704.

The bioactive agent delivery system 700 can also include a DC power supply 708 to power the micropump 704 and microcontroller 706. The bioactive agent delivery system 700 can also include a nozzle 710 coupled to the micropump 704. The nozzle 710 can deliver the bioactive agent pumped by the micropump 704 in the form of microjets. The nozzle 710 may be coupled with the sub-treatment chamber 116. The bioactive agent can, therefore, be sprayed onto the body part of the patient through a nozzle 710. The bioactive agent can be mixed with the warm therapeutic gas provided by the second delivery unit 110. In an example, the bioactive agent is one of insulin, an antibiotic, an anti-aging serum, and a combination thereof.

In another example, the bioactive agent delivery system 700 maybe an independent unit. When the bioactive agent delivery system 700 is an independent unit, only the nozzle 710 of the bioactive agent delivery system 700 may be enclosed within the sub-treatment chamber 116. In an example, the bioactive agent delivery system 700 may be integrated in the gas warmer assembly 102, i.e., placed in a common housing. When the bioactive agent delivery system 700 is included in the common housing, special provision for the bioactive agent container 702, micropump 704, and the microcontroller 706 may be made in the gas warmer assembly 102.

In one example, not illustrated in the figures, the device 100 may be coupled with a Negative Pressure Wound Treatment (NPWT) system to remove exudates during dermatological and sub-cutaneous tissue treatment. Negative-pressure wound therapy (NPWT) is a therapeutic procedure that uses a vacuum dressing to promote healing of acute or chronic wounds. NPWT involves controlled application of negative pressure to a wound environment, using a sealed wound dressing connected to a vacuum pump. Therefore, in the example when the device 100 is coupled with the NPWT system, the NPWT system can include the vacuum dressing and the vacuum pump. The vacuum pump may be switched on during NPWT to remove wound exudates and switched off after NPWT. In one example, NPWT and delivery of warm therapeutic gas can be done simultaneously. In another example, NPWT and delivery of warm therapeutic gas can be done alternately.

Figure 8:
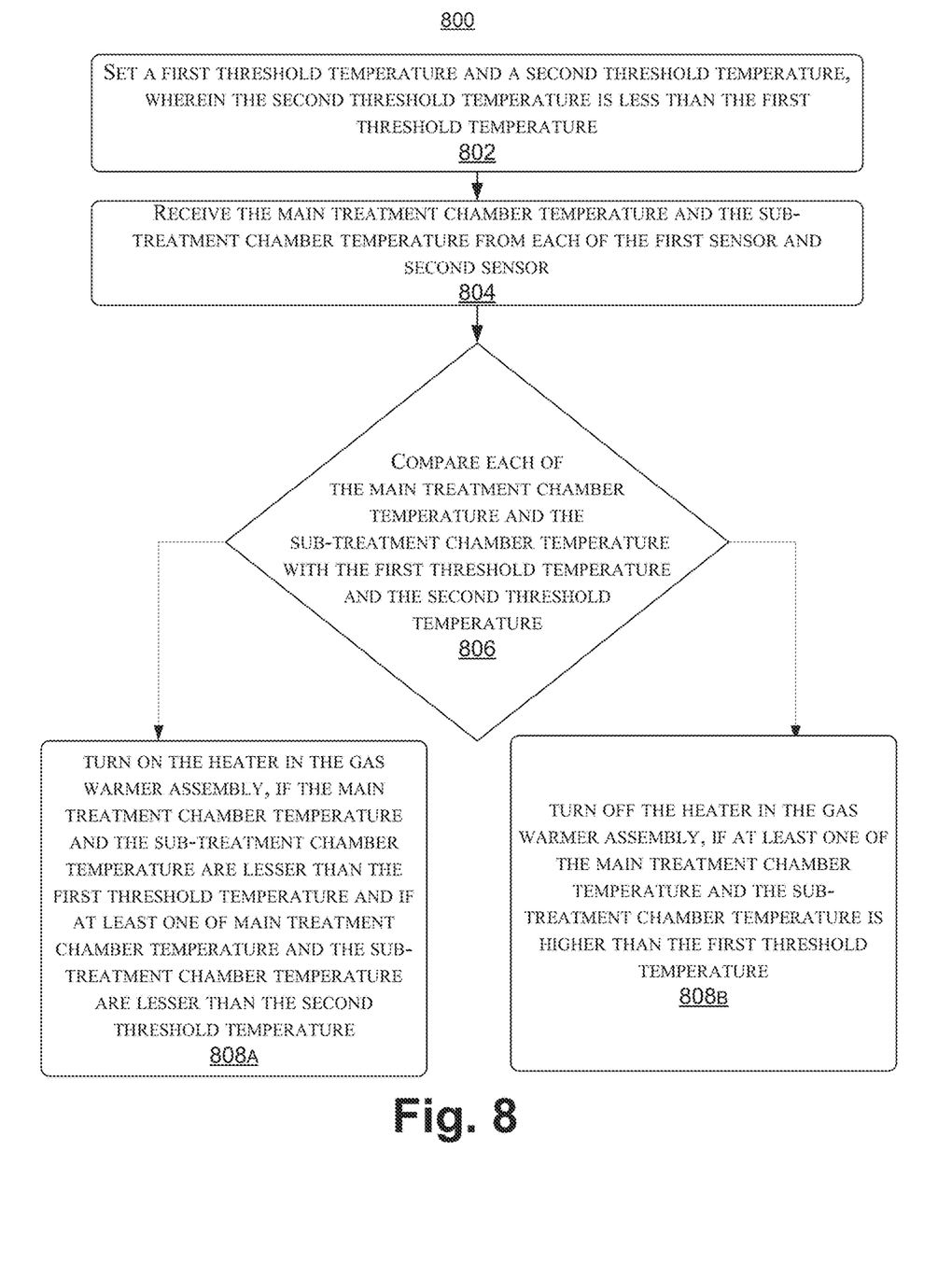
FIG. 8 illustrates operations of a microprocessor to maintain a main treatment chamber temperature and a sub-treatment chamber temperature, in accordance with an implementation of the present subject matter.

In an example, the microprocessor 106 is configured to maintain the first temperature range in the main treatment chamber and the sub-treatment chamber 116. FIG. 8 illustrates example control operations performed by the microprocessor 106. The order in which the operation performed by the microprocessor 106 is described is not intended to be construed as a limitation, and any number of the described blocks can be combined in any order to implement the operation or an alternative operation. Additionally, individual blocks may be deleted as well without departing from the spirit and scope of the subject matter described herein. For discussion, the method 300 is described with reference to the implementations illustrated in FIGS. 1-6.

At block 802, the microprocessor is configured to set the first threshold temperature and a second threshold temperature. The second threshold temperature is less than the first threshold temperature. In one example, the first threshold temperature may be an upper limit of the temperature range of the warm gas that may be used while the second threshold temperature may be a lower limit of the temperature range of the warm gas that may be used. In one example, the first threshold temperature may be 42° C. and the second threshold temperature may be 39° C. In one example, the first threshold temperature and the second threshold temperature may be set using the input module 314 and the set switch 318.

In one example, after the first threshold temperature and the second threshold is set the first sensor 216 and the second sensor 214 can be initialized. In an example, after the first sensor 216 and the second sensor 214 are initialized, the third sensor, the gas warmer inlet sensor, and the gas warmer outlet sensor may be initialized. In one example, each temperature sensor has three pins, i.e., power supply pin, ground pin, and sensor input pin. During initialization of the microprocessor 106, the sensor input pins of the temperature sensors are assigned to appropriate analog input pin of the microprocessor 106.

On setting the first threshold temperature and the second threshold temperature, the microprocessor 106 cyclically performs operations as shown in blocks 804, 806, 808a, and 808b. At block 804, the microprocessor 106 can receive the main treatment chamber temperature and the sub-treatment chamber temperature from each of the first sensor 216 and second sensor 214. At block 806, the microprocessor 106 compares each of the main treatment chamber temperature and the sub-treatment chamber temperature with the first threshold temperature and the second threshold temperature.

Based on the comparing, at step 808a, the microprocessor 106 is configured to turn on the heater 104 in the gas warmer assembly 102, if the main treatment chamber temperature and the sub-treatment chamber temperature are lesser than the first threshold temperature and if at least one of main treatment chamber temperature and the sub-treatment chamber temperature are lesser than the second threshold temperature.

In one example, to provide improved control of temperature in the main treatment chamber 112 and to ensure safety, a third threshold temperature may be set. In said example, the third threshold temperature may be set by the microprocessor 106 based on inputs provided by the operator or the user. The third threshold temperature is greater than the first threshold temperature. Based on the third threshold temperature and the diffuser outlet temperature, the microprocessor 106 may be configured to turn off the heater 104 in the gas warmer assembly 102 when the diffuser outlet temperature is greater than the third threshold temperature. For example, if the main treatment chamber temperature is to be maintained at 42° C., then the third threshold temperature can be set to 70° C. When the diffuser outlet temperature exceeds 70° C., the heater 104 may be switched off.

In an example, at a beginning of the treatment of the patient, based on the diffuser outlet temperature, heating operation of the heater 104 may be turned off for a pre-determined duration until a steady state of the main treatment chamber temperature and the sub-treatment chamber temperature, as measured by the first sensor and the second sensor, is achieved. The microprocessor 106 can be configured to determine, after lapse of the predetermined duration after turning off the heater 104 based on the diffuser outlet temperature, whether the main treatment chamber temperature and the sub-treatment chamber temperature are in the first temperature range. For example, when the diffuser outlet temperature exceeds the third threshold temperature, the heater 104 may be switched off for a period of 3-5 minutes to allow the main treatment chamber temperature and sub-treatment chamber temperature to heat up to a temperature in the first temperature range. Further, if after the pre-determined duration, the main treatment chamber temperature and sub-treatment chamber temperature are not in the first temperature range, the microprocessor 106 can be configured to switch on the heater 104.

The microprocessor 106 can further be configured to repeat the steps of turning off the heater 104 and switching on the heater 104 based on the main treatment chamber temperature and the sub-treatment chamber temperature until a condition is fulfilled. The condition may be one of a number of times the heater is turned off, a pre-determined period, and main treatment chamber temperature and the sub-treatment chamber temperature being in the first temperature range. For example, the microprocessor 106 may be configured to count number of times the heater 104 may be turned off. If after turning off the heater n-times the main treatment chamber temperature and sub-treatment chamber temperature do not increase to the temperature in the first temperature range, the microprocessor 106 may be configured to provide a device malfunction alarm. Similar, turning off the heater 104 and switching on the heater 104 can be done for a pre-determined period. If after elapse of the pre-determined period, the main treatment chamber temperature and sub-treatment chamber temperature do not increase to the temperature in the first temperature range, the microprocessor 106 may be configured to provide a device malfunction alarm.

The present subject matter, therefore, provides a device for delivery of warm therapeutic gas. By using the sub-treatment chamber enclosed in the main treatment chamber for the treatment, quantity of therapeutic gas can be substantially reduced. For example, if only the main treatment chamber was used for the treatment, the amount of therapeutic gas, namely, warm oxygen required for a 35 minutes treatment cycle was found to be 35 liters. However, by using the sub-treatment chamber, it was found that the amount of warm oxygen required was reduced to 2-3 liters. Further, as the amount of therapeutic gas required was reduced, treatment time could be increased without substantial increase in cost of treatment.

The present subject matter will now be illustrated with working examples, which are intended to illustrate the working of disclosure and not intended to be taken restrictively to imply any limitations on the scope of the present disclosure. Unless defined otherwise, all technical and scientific terms used herein have the same meaning as commonly understood to one of ordinary skill in the art to which this disclosure belongs. It is to be understood that this disclosure is not limited to the particular methods and experimental conditions described, as such methods and conditions may vary depending on the process and inputs used as will be easily understood by a person skilled in the art.

EXAMPLES

Clinical Study

In this example, a prospective observational randomized trial was performed with blinded end point analysis to assess among patients with diabetic foot ulcers (Wagner-Meggit grade II/III), the efficacy of topical warm oxygen therapy on top of standard of care compared with standard care alone on the wound healing rate.

Selected patients were randomized into two cohorts, control group and test group. Patients in control group were provided standard wound care three times a week for 6 weeks while patients in test group were provided with standard wound care and the warm oxygen therapy of the present subject matter.

Rate of wound healing based on wound size (area) was measured using imaging techniques and software analysis. Minimum and maximum area of the wound was measured at the beginning, referred to as baseline, of the clinical study. Total duration of treatment and observation was 6 weeks. Overall, warm oxygen therapy was well tolerated by patients, without any reported discomfort, adverse events or serious adverse events. Further, ulcer healing rates appeared to have improved among patients receiving the warm oxygen therapy on top of standard care.

Although the subject matter has been described in considerable detail with reference to certain examples and implementations thereof, other implementations are possible. As such, the present subject matter should not be limited to the description of the preferred examples and implementations contained therein.

We claim:

1. A device for delivery of warm therapeutic gas, the device comprising:
   a gas warmer assembly to warm a first gas to a temperature in a first temperature range to obtain a warm first gas, wherein the gas warmer assembly comprises:
      a heater to warm the first gas to the temperature in the first temperature range; and
      a microprocessor to control the heater;
   a first delivery unit coupled to the gas warmer assembly to deliver the warm first gas received from the gas warmer assembly to a main treatment chamber;
   a second delivery unit configured to receive a therapeutic gas from a gas supply, wherein the second delivery unit comprises:
      a first portion that substantially passes through the first delivery unit, wherein the warm first gas warms the therapeutic gas in the first portion to obtain a warm therapeutic gas; and
      a second portion configured to deliver the warm therapeutic gas to a sub-treatment chamber;
   wherein the main treatment chamber is associated with a first sensor to measure and communicate a main treatment chamber temperature to the microprocessor; and
   wherein the sub-treatment chamber is configured to enclose a site for treatment, wherein the main treatment chamber encloses the sub-treatment chamber to retain heat in the sub-treatment chamber, and wherein the sub-treatment chamber is associated with a second sensor to measure and communicate a sub-treatment chamber temperature to the microprocessor.

2. The device of claim 1, wherein the device comprises a remote-control unit operably connected with the microprocessor to control parameters of the gas warmer assembly based on user input.

3. The device of claim 1, wherein the gas warmer assembly comprises:
   a gas warmer inlet, associated with a gas warmer inlet temperature sensor, to receive the first gas, wherein the gas warmer inlet temperature sensor measures an inlet temperature of the first gas at the gas warmer inlet and provides the inlet temperature to the microprocessor;
   an input module to receive input parameters, wherein the input parameters comprise a threshold temperature at which the main treatment chamber temperature and the sub-treatment chamber temperature are to be maintained;
   a display mounted on the gas warmer assembly to display values of input and measured parameters; and
   a gas warmer outlet, associated with a gas warmer outlet temperature sensor, to provide the warm first gas from the gas warmer outlet, wherein the gas warmer outlet temperature sensor measures an outlet temperature of the warm first gas at the gas warmer outlet and provides the outlet temperature to the microprocessor.

4. The device of claim 1, wherein the gas warmer assembly comprises:
   a buzzer to provide an alarm when at least one of the main treatment chamber temperature and the sub-treatment chamber temperature measured by the first sensor and the second sensor is more than a first threshold temperature; and
   a fan to draw the first gas into the gas warmer assembly.

5. The device of claim 1, wherein the heater is a Nichrome heating element.

6. The device of claim 1, wherein the heater comprises:
   a heater inlet to receive the first gas from the gas warmer inlet;
   a coil slot sandwiched between two aluminum plates, wherein the coil slot comprises a copper coil to receive the first gas from the heater inlet and to allow flow of the first gas through the copper coil;
   a heating element, wherein the aluminum plates with the coil slot sandwiched therebetween are stacked over the heating element, wherein the heating element warms the first gas flowing through the copper coil;
   another aluminum plate, wherein the heating element is stacked over the another aluminum plate; and
   a heater outlet, to provide the warm first gas from the heater.

7. The device of claim 1, wherein the heater comprises:
   a heater inlet to receive the first gas;
   a copper coil to receive the first gas from the heater inlet and to allow flow of the first gas through the copper coil;
   a heating element, wherein the heating element warms the first gas flowing through the copper coil;
   an insulating jacket enclosing the copper coil and the heating element; and
   a heater outlet, to provide the warm first gas from the heater.

8. The device of claim 1, wherein the heater comprises:
   a heater inlet to receive the first gas;
   a copper coil to receive the first gas from the heater inlet and allow flow of the first gas through the copper coil;
   a heating element, wherein the heating element warms the first gas flowing through the copper coil;
   an insulating box enclosing the copper coil and the heating element; and
   a heater outlet, to provide the warm first gas from the heater.

9. The device of claim 1, wherein the heater is one of an electric heater, a conduction heater, a convection heater, or a radiation heater.

10. The device of claim 1, wherein the first delivery unit comprises:
    a tube having a first end coupled to the gas warmer assembly to receive the warm first gas from the gas warmer assembly and a second end enclosed in the main treatment chamber; and a diffuser provided on the second end of the tube to diffuse the warm first gas in the main treatment chamber, wherein the diffuser is associated with a third temperature sensor to measure and communicate a diffuser outlet temperature to the microprocessor.

11. The device of claim 10, wherein the microprocessor is configured to maintain the first temperature range in the main treatment chamber and the sub-treatment chamber, wherein the microprocessor is configured to:
set a first threshold temperature and a second threshold temperature, wherein the second threshold temperature is less than the first threshold temperature; and
cyclically:
receive the main treatment chamber temperature and the sub-treatment chamber temperature from the first sensor and the second sensor, respectively;
compare each of the main treatment chamber temperature and the sub-treatment chamber temperature with the first threshold temperature and the second threshold temperature, wherein the microprocessor is further configured to:
turn on the heater in the gas warmer assembly, if the main treatment chamber temperature and the sub-treatment chamber temperature are less than the first threshold temperature and if at least one of the main treatment chamber temperature or the sub-treatment chamber temperature is less than the second threshold temperature; and
turn off the heater in the gas warmer assembly, if at least one of the main treatment chamber temperature or the sub-treatment chamber temperature is higher than the first threshold temperature.

12. The device of claim 11, wherein the microprocessor is configured to:
set a third threshold temperature, wherein the third threshold temperature is greater than the first threshold temperature, and wherein based on the diffuser outlet temperature, the microprocessor is further configured to:
turn off the heater in the gas warmer assembly when the diffuser outlet temperature is greater than the third threshold temperature.

13. The device of claim 12, wherein the microprocessor is configured to:
determine, after lapse of a predetermined duration after turning off the heater based on the diffuser outlet temperature, whether the main treatment chamber temperature and the sub-treatment chamber temperature are in the first temperature range;
switch on the heater of the gas warmer assembly when the main treatment chamber temperature and the sub-treatment chamber temperature are not in the first temperature range; and
repeat steps of turning off the heater and switching on the heater based on the main treatment chamber temperature and the sub-treatment chamber temperature until a condition is fulfilled, wherein the condition is one of a number of times the heater is turned off, a pre-determined period, or the main treatment chamber temperature and the sub-treatment chamber temperature being in the first temperature range.

14. The device of claim 1, wherein the device comprises a bioactive agent delivery system, the bioactive agent delivery system comprising:
a bioactive agent container to hold a bioactive agent;
a micropump to pump the bioactive agent from the bioactive agent container;
a microcontroller, wherein the microcontroller controls the micropump to pump metered doses of the bioactive agent; and
a nozzle coupled to the micropump to deliver the bioactive agent as microjets, wherein the nozzle is configured for coupling with the sub-treatment chamber.

15. The device of claim 14, wherein the bioactive agent is one of insulin, an antibiotic, an anti-aging serum, or a combination thereof.

16. The device of claim 1, wherein the device comprises a Negative Pressure Wound Treatment (NPWT) system to remove exudates during delivery of the warm therapeutic gas.

17. The device of claim 1, wherein the main treatment chamber and the sub-treatment chamber are formed from a treatment bag and wherein the treatment bag encloses a body part of a patient.

18. The device of claim 17, wherein the treatment bag comprises a plurality of shape retainers that hold a therapy bag in shape and prevent it from collapsing.

19. The device of claim 1, wherein the first gas is air and the therapeutic gas comprises a gas selected from the group consisting of oxygen, ozone, and a combination thereof.

* * * * *